United States Patent [19]
Navarro

[11] Patent Number: 5,861,369
[45] Date of Patent: Jan. 19, 1999

[54] (2-CARBOXY-3-HYDROXY-PROPYL)-IMINODIACETIC ACID AND DERIVATIVES

[75] Inventor: Charles Navarro, Twello, Netherlands

[73] Assignee: Akzo Nobel nv, Arnhem, Netherlands

[21] Appl. No.: 549,853

[22] PCT Filed: May 11, 1994

[86] PCT No.: PCT/EP94/01561

§ 371 Date: Feb. 29, 1996

§ 102(e) Date: Feb. 29, 1996

[87] PCT Pub. No.: WO94/26691

PCT Pub. Date: Nov. 24, 1994

[30] Foreign Application Priority Data

May 19, 1993 [EP] European Pat. Off. ............ 93201430

[51] Int. Cl.$^6$ ............................ C07C 229/22; C11D 3/33
[52] U.S. Cl. ........................ 510/490; 510/488; 510/489; 510/494; 510/499; 558/451; 562/104; 562/107; 562/512; 562/553
[58] Field of Search ................................ 510/490, 488, 510/489, 494, 499

[56] References Cited

U.S. PATENT DOCUMENTS

| | | | |
|---|---|---|---|
| 4,827,014 | 5/1989 | Baur et al. ............................. | 538/441 |
| 4,973,730 | 11/1990 | Baur et al. ............................. | 558/372 |
| 5,019,296 | 5/1991 | Baur et al. ............................. | 252/546 |
| 5,082,599 | 1/1992 | Oftring et al. ......................... | 252/546 |
| 5,112,530 | 5/1992 | Baur et al. ............................. | 252/548 |
| 5,208,369 | 5/1993 | Crump et al. .......................... | 562/106 |
| 5,258,141 | 11/1993 | Crump et al. .......................... | 252/546 |

FOREIGN PATENT DOCUMENTS 0 516 102   12/1992   European Pat. Off. ...... C07C 309/14

OTHER PUBLICATIONS

CAS No. 98768–24–2 Registry.
CAS No. 98768–23–1 Registry.
Sayo et al, Chem. Abstract 113: 190758a, "Preparation of Optically active 3–hydroxybutanoic acid amidoesters", 1990.

Murata et al, Chem. Abstract 117: 171077u, "Preparation of 3–(tetrahydropyrimah–5–yl)carbapenms as Antimicrobals", 1992.

Bebkon et al, Chem. Abstract 117: 234,490w, 1992.

Murayama et al, Chem. Abstract 117: 90044d, 1992.

*Primary Examiner*—Ellen M. McAvoy
*Attorney, Agent, or Firm*—Ralph J. Mancini

[57] ABSTRACT

The present invention relates to compounds of the formula 1

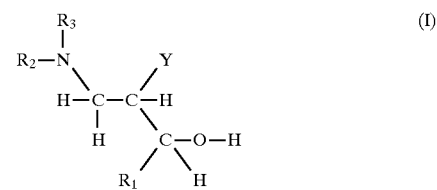

wherein $R_1$ is selected from hydrogen and $-R_4-R_5$ where $R_4$ is selected from nothing $C_1-C_{20}$ linear or branched alkylene $C_3-C_{20}$ cycloalkylene, $C_6-C_{20}$ arylene, $C_7-C_{20}$ alkarylene and $C_7-C_{20}$ arlkylene; and $R_5$ is one of hydrogen, hydroxy, $-CO_2Z$, phenyl hydroxyphenyl pyridyl, nitrophenyl, furyl, and thienyl; $R_2$ and $R_3$ are independently selected from a group of the formula $-R_4-R_6$; where $R_4$ is as defined above and $R_6$ is one of hydrogen, hydroxy $-CO_2Z$. $-CH(CO_2Z)-CH_2-CO_2Z$ and $NR_7R_8$; where $R_7$ and $R_8$ are independently selected from a group of the formula: $-(CH_2)k-R_g$: where k=0–20 and $R_g$ is one of hydrogen, hydroxy, $-CO_2Z$. and $-CH(CO_2Z)-CH_2-CO_2Z$: wherein Y is selected from $-CO_2Z$. $-SO_3Z$ and $-C\equiv N$: and wherein each Z is independently selected from hydrogen, alkali metal, ammoniumr and substituted ammonium, to processes for making these compounds, and to the use of these compounds in a variety of applications involving chelating or sequestration.

15 Claims, No Drawings

(2-CARBOXY-3-HYDROXY-PROPYL)-IMINODIACETIC ACID AND DERIVATIVES

BACKGROUND OF THE INVENTION

The present invention relates to (2-carboxy-3-hydroxy-propyl) -iminodiacetic acid and derivatives thereof. The present invention also relates to a process for the preparation of such compounds and their use as sequestering agents.

2—hydroxy—3—aminopropignic—N,N—diacetic acid and its derivatives are known from U.S. Pat. No. 4,827,014. Though these compounds are similar to the compounds of the present invention, they are structurally different and, as a result, the compounds of the present invention exhibit superior properties. This U.S. Patent also discloses a method for making these compounds, which method is significantly different than the method of the present invention. Finally, this patent points out that these compounds are useful as complexing agents, bleaching agent stabilizers and builders for washing and cleaning compositions.

U.S. Pat. No. 5,112,530 also discloses 2—hydroxy—3—aminopropionic acid derivatives and their use as complexing agents, bleach stabilizers and builders in detergent compositions.

U.S. Pat.No. 5,082,599 discloses 2—methyl—and 2—hydroxymethyl-serine —N,N—diacetic acid and derivatives thereof, and their use as complexing agents for heavy metal ions or alkaline earth metal ions and as bleach stabilizers or builders in detergents and cleaning formulations.

U.S. Pat. Nos. 5,019,296 and 4,973,730 also relate to the serine—N,N—diacetic acid and its derivatives, as well as methods for their preparation. Again, these compounds are used as complexing agents in detergent compositions.

The article, "Herstellung Einiger Neuer Komplexbildender Verbindungen und Bestimmung Ihrer Konstanten," Erdey, L. et al, Acta Chim. Hung. Tomus, 21, pp. 327–332 (1959) discloses a method for preparing the complexing agents OL—Serine—N—diacetic acid and L—Glutaminic acid—N—diacetic acid and the measurement of the dissociation constants thereof.

Published European patent application 0 516 102 discloses biodegradable chelants comprising sulfonate groups and compositions thereof. Typical compounds include glycine—N—2—hydroxyethyl—N—2—hydroxypropyl sulfonic acid and nitrilo—N,N—bis(carboxymethyl)—N—2—hydroxypropyl sulfonic acid. Also disclosed are numerous uses for biodegradable chelants. The sulfonic acids, salts and complexes, as disclosed, are not subject matter of the current invention.

Finally, 2—((((1,1—dimethylethoxy)carbonyl)(phenylmethyl)amino)methyl) —3—hydroxy butanoic acid is known from Chemical Abstract No. 98768—24—2 , and a-((((1,1—dimethylethoxy)carbonyl)(phenylmethyl)amino)methyl)—β—hydroxy—benzenepentanoic acid is known from Chemical Abstract No. 98768—23—1. These materials are significantly different from the materials of the present invention since they contain a phenylmethyl substituent substituted on the nitrogen atom.

While the foregoing publications disclose several compounds which are useful as sequestering agents, none of these materials combines a high level of activity as a sequestering agent with a good biodegradability. Accordingly, the primary object of the present invention is to provide novel compounds which are biodegradable and which exhibit excellent sequestering capabilities.

The foregoing sequestering agents also suffer from the disadvantage that they require complex synthesis processes which make them impractical for large-scale commercialization. Accordingly, it is a further object of the present invention to provide a method for making biodegradable sequestering agents which is simple and which can be scaled up for large-scale production.

These and other objects of the invention will be apparent to the man of skill in the art from the summary and detailed description which follow.

SUMMARY OF THE INVENTION

In a first aspect, the present invention relates to compounds of the formula I:

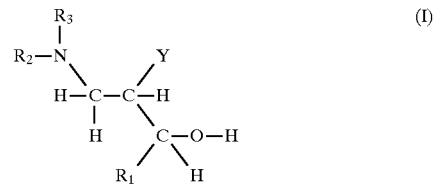

wherein $R_1$ is selected from hydrogen and —$R_4$—$R_5$; where $R_4$ is selected from nothing, $C_1$—$C_{20}$ linear or branched alkylene, $C_3$—$C_{20}$ cycloalkylene, $C_6$-$C_{20}$ arylene, $C_7$-$C_{20}$ alkarylene and $C_7$-$C_{20}$ aralkylene; and $R_5$ is one of hydrogen, hydroxy, —$CO_2Z$, phenyl, hydroxyphenyl, pyridyl, nitrophenyl, furyl and thienyl; $R_2$ and $R_3$ are independently selected from a group of the formula —$R_4$—$R_6$; where $R_4$ is as defined above and $R_6$ is one of hydrogen, hydroxy, —$CO_2Z$, —$CH(CO_2Z)$—$CH_2$—$CO_2Z$ and $NR_7R_8$; where $R_7$ and $R_8$ are independently selected from a group of the formula: —$(CH_2)k$—$Rg$; where $k=0$–$20$ and $Rg$ is one of hydrogen, hydroxy, —$CO_2Z$, and —$CH(CO_2Z)$—$CH_2$—$CO_2Z$; wherein Y is selected from —$CO_2Z$ and —C≡N; and wherein each Z is independently selected from hydrogen, alkali metal, ammnonium and substituted ammonium. These compounds are biodegradable and exhibit unexpectedly good activity as complexing and/or sequestering agents.

In a second aspect, the present invention relates to a process for the production of the compounds of the formula I including the steps of:

(a) reacting an amine of the formula $R_2R_3NH$, wherein $R_2$ and $R_3$ are as defined above, with a compound of the formula II:

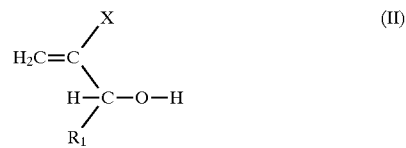

wherein $R_1$ is as defined above; and X is an electron withdrawing group which activates the double bond for an addition reaction;

(b) optionally hydrolyzing the group X to provide a carboxylic acid group or a salt thereof; and (c) optionally neutralizing said carboxylic acid group with an alkali metal or ammonium.

This relatively simple process can be scaled-up for large-scale commercial production more easily than comparable prior art processes for making similar complexing agents.

In a third aspect, the present invention relates to the use of compounds of the formula I as a complex forming agent for heavy metals and/or alkaline earth metal ions, as a builder in washing and cleaning compositions and as a bleaching agent stabilizer in washing and cleaning compositions.

In a fourth aspect, the present invention relates to chelates of the compounds of the formula I which are useful, for example, for the removal of hydrogen sulfide from gas streams.

DETAILED DESCRIPTION OF THE PREFERRED EMBODIMENTS

In a first aspect, the present invention relates to compounds represented by the general formula I:

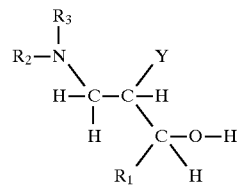

(I)

wherein $R_1$ is selected from hydrogen and $-R_4-R_5$; where $R_4$ is selected from nothing, $C_1-C_{20}$ linear or branched alkylene, $C_3-C_{20}$ cycloalkylene, $C_6-C_{20}$ arylene, $C_7-C_{20}$ alkarylene and $C_7-C_{20}$ aralkylene; and $R_5$ is one of hydrogen, hydroxy, $-CO_2Z$, phenyl, hydroxyphenyl, pyridyl, nitrophenyl, furyl and thienyl; $R_2$ and $R_3$ are independently selected from a group of the formula $-R_4-R_6$; where $R_4$ is as defined above and $R_6$ is one of hydrogen, hydroxy, $-CO_2$ Z, $-CH(CO_2Z)-CH_2-CO_2$ Z and $NR_7R_8$; where $R_7$ and $R_8$ are independently selected from a group of the formula: $-(CH_2)k-R_9$; where $k=0-20$ and $R_9$ is one of hydrogen, hydroxy, $-CO_2Z$, and $-CH(CO_2Z)-CH_2-CO_2Z$; wherein Y is selected from $-CO_2Z$, $SO_3Z$ and $-C\equiv N$; and wherein each Z is independently selected from hydrogen, alkali metal, ammonium and substituted ammonium.

These compounds are useful as complexing agents for heavy metal ions and/or alkaline earth metal ions, as sequestering agents, as stabilizers for bleaching compositions and as builders for washing and cleaning compositions. Other suitable uses include industrial cleansers, electroplating, photographic bleach baths, water treatment, paper industry and cosmetics, among others. Further details of such uses of the present compounds can be found in the patent documents mentioned above and, in particular, European patent application 0 516 102, the disclosure of which is hereby incorporated by reference.

The compounds may be in the form of free carboxylic acids (Z=H) or partially or completely in their salt form. In the latter case, Z is an alkali metal ion such as lithium, sodium or potassium or Z may be an ammonium or a substituted ammonium ion such as dimethyl ammonium, and diethyl ammonium. In the case where Z is an ammonium ion, the ammonium ion may be partially or completely substituted by $C_1-C_4$ alkyl groups or $C_1-C_4$ hydroxyalkyl groups. Examples of such materials include the triamine salts based on amine bases such as trialkylamines and trialkanolamines.

As preferred complexing agents of the formula I are those where $R_1$ is hydrogen and $R_2$ and $R_3$ are $-CH_2-CO_2Z$, Y is $-CO_2Z$ and where Z is either hydrogen, an alkali metal salt or ammonium. Even more preferred are the complexing agents where Z is hydrogen.

As specific examples of preferred compounds may be mentioned (2—carboxy—3—hydroxypropyl) iminodiacetic acid, 2—carboxy—3—hydroxybutyl iminodiacetic acid, 2—carboxy—3—hydroxy—3—phenylpropyl iminodiacetic acid and 2—carboxy—3—hydroxy—3—furylpropyl iminodiacetic acid.

In a second aspect, the present invention relates to a process for the preparation of compounds of the formula I.

In particular, compounds of the formula I can be prepared by reacting an amine of the formula $R_2R_3NH$, wherein $R_2$ and $R_3$ are as defined above, with a compound of the formula II:

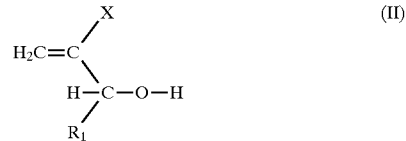

(II)

wherein $R_1$ is as defined above; and X is an electron withdrawing group which activates the double bond for an addition reaction; optionally hydrolyzing the group X to provide a carboxylic acid group; and optionally neutralizing said carboxylic acid group with an alkali metal or ammonium salt group as mentioned above.

The reaction between the amine and the compound of the formula II is preferably carried out at a temperature of 10–100°C. and the amine and compound of the formula II are preferably reacted in equimolar amounts, though under specific circumstances, this may be varied.

Preferred amines for use in the process include iminodiacetic acid, the mono- and disodium salts thereof, the potassium or ammonium salts, iminodiacetonitrile, methyliminodiacetate and ethyl iminodiacetate.

The compound of the formula II can be obtained by the reaction as follows. A compound of the formula III is reacted with a compound of the formula IV to produce the compound of the formula II.

(III)

wherein X is as defined for the formula II.

(IV)

wherein $R_1$ is as defined for the formula II. An example of a compound of the formula II which can be used in the process of the present invention is ethyl—2—hydroxymethylacrylate.

The reaction between the amine and the compound of the formula II is preferably carried out in an aqueous media and at an alkaline pH. Upon completion of the reaction, the reaction mixture is brought to room temperature and acidified. The solvent can then be distilled off leaving the desired product.

Optionally, the product of the reaction of the amine and the compound of the formula II may be alkylated using conventional alkylation techniques prior to during or after hydrolysis.

The hydrolysis of the nitrile group and of any amide or ester groups present is conveniently carried out at 20 –110°C, preferably at 40–100°C in the presence of a small excess of either acid or base.

In addition, the carboxylic acid group formed by the hydrolysis step may be optionally substituted with an alkali metal or ammonium to form an acid salt of the compound of the formula I. This can be accomplished by treating the compound of the formula I with an alkali metal or ammonium salt.

The process of the present invention has the advantage that it leads to a high yield of the desired product.

In a further aspect, the present invention relates to the use of compounds of the formula I a complex forming agent for heavy metals and/or alkaline earth metal ions, as a builder in washing and cleaning compositions, as a bleaching agent stabilizer in washing and cleaning compositions, in photofinishing, in heavy metal plating, in heavy metal deactivation and for the prevention of scale, among other uses. Details regarding such uses can be found in the patent publications mentioned above, which details are hereby incorporated by reference herein.

In a final aspect, the present invention relates to chelates of compounds of the formula I with iron, calcium, magnesium, zinc, copper, manganese, aluminum and barium.

The following examples are presented to further illustrate the invention.

Example 1

Synthesis of (2—Carboxy—3—hydroxypropyl) iminodiacetic acid (CHPIDA) 6.65 g. (0.05 mole) of iminodiacetic acid were suspended in 25 ml of water and neutralized with sodium hydroxide to pH=10–12. 6.5 g. (0.05 mole) of ethyl—2—hydroxymethylacrylate was added dropwise to the solution and the temperature of the resulting mixture increased to 80°C. The pH was maintained at 10–12 by further addition of sodium hydroxide. The reaction mixture was stirred at 80°C for 20 hours and then cooled to room temperature and acidified to pH=1.5 with concentrated hydrochloric acid. The solvent was distilled under reduced pressure to half the weight of the solution and the product was allowed to crystallize. The white precipitate was filtered, washed with water and methanol and then dried in a vacuum to 5.3 g. of white powder. The yield was 45% of theoretical and the product had a melting point of 195 °C.

Example 2

Hydrogen Peroxide Stabilization with CHPIDA

A. Measurement of hydrogen peroxide concentrations of 0–1%.

With a diluter set to dilute 96 µl to 15 ml, a sample of 96 µl of hydrogen peroxide solution was taken. The solution was placed in the stirred beaker with a color reagent obtained by diluting 173 g. sulfuric acid and 45 ml of 15% w/v $Ti(SO_4)_2$ solution up to 500 ml with demineralized water to give a stock solution and then further diluting 58.5 ml of the stock solution to 1 liter with demineralized water. 15 ml of a yellow colored mixture was obtained. This mixture was drawn through a cuvette and the absorbency was measured to determine the hydrogen peroxide concentration.

B. Hydrogen Peroxide Stabilization Test

Fourteen polyethylene bottles were filled with 5.0 ml of a metal solution containing 20 ppm Cu(II), 40 ppm Fe(III) and 50 ppm Mn(II). One control bottle was filled with water. To all of these bottles except one was added 5.0 ml of sequestering agent solution containing 0.5 w/w% CHPIDA in demineralized water and 10.0 ml of sodium p- phenolsulphonate solution (0.1 M). The total weight of the solution was brought to 30 g. using additional demineralized water. The pH was then adjusted to 9.5 with either sodium hydroxide or hydrochloric acid, as needed. The total weight of the solutions was then brought to 45 g. with additional demineralized water. To these solutions, 5.0 ml of 10% hydrogen peroxide solution was added.

This produced solutions containing 2 ppm Cu(II), 4 ppm Fe(III), 5 ppm Mn(II), 0.05% sequestering agent, 0.02 M sodium p-phenolsulphonate and 1% by weight of hydrogen peroxide.

The bottles were inserted in a heating bath and shaken at 50°C (120 rpm). Each half hour a sample was taken quickly and inserted into a numbered standby bottle. From the samples, the hydrogen peroxide content was determined using the method described above. The results are given in Table 1.

TABLE 1

| Sequestering Agent | % Peroxide Remaining in Solution | | | |
|---|---|---|---|---|
| | 30 min | 60 min. | 90 min. | 120 min. |
| CHPIDA | 81 | 74 | 63 | 57 |
| ISDA | 87 | 55 | 31 | 19 |

ISDA is 2-hydroxy-3-aminopropionic-N,N-diacetic acid.

This example demonstrates that CHPIDA, a compound in accordance with the present invention, is unexpectedly superior to ISDA, the closest prior art compound, in hydrogen peroxide stabilization. Hydrogen peroxide stabilization is a good indication of the chelating ability of the present compounds.

Example 3

Synthesis of (2—Carboxy—3—hydroxybutyl) iminodiacetic acid 13.3 g. (0.1 mole) of iminodiacetic acid were suspended in 100 ml. of water and neutralized with sodium hydroxide to pH=10–12. 14.4 g (0.1 mole) ethyl——2—(1—hydroxyethyl)propenoate was added and the pH was maintained at 10–12 by further addition of sodium hydroxide. The reaction mixture was stirred at 80°C for 20 hours and then cooled at room temperature and acidified to pH=2. The solvent was distilled under reduced pressure to one-third of the weight of the solution and sodium chloride was filtered off. The filtrate was poured in 400 ml. of methanol/acetone (50/50) and the precipitate was washed with acetone and dried in vacuum to 12.3 g of a white powder. The yield was 49% of theoretical.

Example 4

Preparation of CHPIDA-Fe(III) Chelate 40.4 g (0.1 mole) of $Fe(NO_3)_3 \cdot 9H_2O$ were dissolved in 200 ml of demineralized water, 25.85 g (0.11 mole) of CHPIDA were added and the mixture was neutralized with ammonium hydroxide. Sufficient water was added to produce 300 ml of a dark solution of the Fe(III) chelate of CHPIDA.

The foregoing examples have been presented for the purposes of illustration and description only and are not to be construed as limiting the invention in any way. The scope of the invention is to be determined from the claims appended hereto.

What is claimed is:

1. A compound represented by the formula I:

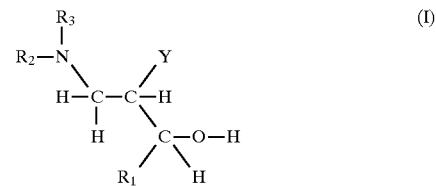

wherein $R_1$ is selected from hydrogen or —$R_4$—$R_5R_4$ is selected from nothing, $C_f$—$C_{20}$ linear or branched alkylene, $C_3$—$C_{20}$ cycloalkylene, $C_6$—$C_{20}$ arylene, $C_7$—$C_{20}$ alkarylene or $C_7$—$C_{20}$ aralkylene; $R_5$ is selected from hydrogen, hydroxy, —CO$_2$Z, phenyl, hydroxyphenyl, pyridyl, nitrophenyl, fura or thienyl; R$_2$ and R$_3$ are independently selected from a group of the formula -R$_4$—R$_6$ where R$_4$ is as defined above and R$_6$ is selected from hydrogen, hydroxy, —CO$_2$Z, —CH(CO$_2$Z)—CH$_2$—CO$_2$Z or NR$_7$R$_8$ where R$_7$ and R$_8$ are independently selected from a group of the formula: —(CH$_2$)k—R$_9$ ; where k=0–20 and R$_9$ is selected from hydrogen, hydroxy, -CO$_2$Z and –CH(CO$_2$Z)–CH$_2$Z; wherein Y is selected from -CO$_2$Z, —SO$_3$Z and -C≡N; and wherein each Z is independently selected from hydrogen, alkali metal, ammonium or substituted ammonium.

2. The compound of claim 1 where each Z is hydrogen.

3. The compound of claim 1 wherein R$_1$ is hydrogen and R$_2$ and R$_3$ are —CH$_2$—CO$_2$Z.

4. A process for the production of the compound of claim 1 which comprises the steps of:
 (a) reacting an amine of the formula R$_2$R$_3$NH, or alkali metal or ammonium salt thereof, wherein R$_2$ and R$_3$ are as defined in claim 1 with a compound of the formula II:

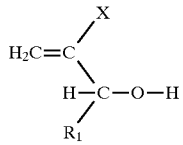 (II)

wherein R$_1$ is as defined in claim 1 and X is an electron withdrawing group which activates the double bond for an addition reaction;
 (b) optionally hydrolyzing the group X to provide a carboxylic acid group or a salt thereof; and
 (c) optionally neutralizing said carboxylic acid group with an alkali metal or ammonium.

5. The process of claim 4 which further comprises the step of alkylating the amine obtained from step (a).

6. The process of claim 4 which further comprises the step of reacting a compound of the formula III:

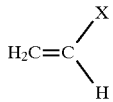 (III)

wherein X is as defined in claim 4 with a compound of the formula IV:

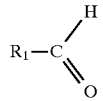 (IV)

wherein R$_1$ is as defined in claim 4 to produce a compound of the formula II.

7. The process of claim 4 wherein X is an ester group or a nitrile group.

8. A complex forming agent for heavy metals and/or alkaline earth metal ions which comprises at least one compound of claim 1.

9. A builder in washing and cleaning compositions which comprises at least one compound of claim 1.

10. A bleaching agent stabilizer which comprises at least one compound of claim 1.

11. A chelate of the compound of claim 1 with one or more metals selected from iron, calcium, magnesium, zinc, copper, manganese, aluminium and barium.

12. The chelate of claim 11 wherein the metal is selected from iron, calcium, mangnesium, zinc and copper.

13. A gas sweetening agent which comprises at least one chelate in accordance with claim 11.

14. A compound represented by the formula:

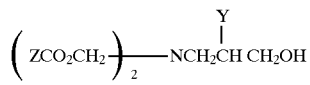

wherein Y is selected from —CO$_2$Z, —SO$_3$Z and —C≡N; and wherein each Z is independently selected from hydrogen, alkali metal, ammonium or substituted ammonium.

15. A process for the production of a compound represented by the formula I:

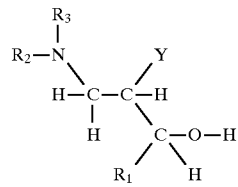 (I)

wherein R$_1$ is selected from hydrogen or R$_4$—R$_5$; R$_4$ is selected from nothing, C$_1$—C$_{20}$ linear or branched alkylene, C$_3$—C$_{20}$ cycloalkylene, C$_6$—C$_{20}$ arylene, C$_7$—C$_{20}$ alkarylene or C$_7$-C$_{20}$ aralkylene; R$_5$ is selected from hydrogen, hydroxy, —CO$_2$Z, phenyl, hydroxyphenyl, pyridyl, nitrophenyl, furyl or thienyl; R$_2$ and R$_3$ are independently selected from a group of the formula -R4-R6 where R$_4$ is as defined above and R6 is selected from hydrogen, hydroxy, - CO$_2$Z, —CH(—CO$_2$Z)—CH$_2$—CO$_2$Z or NR$_7$R$_8$ where R$_7$ and R$_8$ are independently selected from a group of the formula: —(CH$_2$)k—R$_9$; where k=0–20 and R$_9$ is selected from hydrogen, hydroxy, - CO$_2$Z and —C≡N; wherein Y is selected from —CO$_2$Z —SO$_3$ and —C≡N; and wherein each Z is independently selected from hydrogen, alkali metal, anmonium or substituted ammonium, the process comprising the steps of:
 (a) reacting an amine of the formula R$_2$R$_3$NH, or an alkali metal or ammonium salt thereof, wherein R$_2$ and R$_3$ are as defined above, with a compound of the formula II:

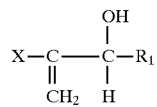

wherein R$_1$ is as defined above and X is an electron withdrawing group which activates the double bond for an additional reaction;
 (b) optionally hydrolyzing the group X to provide a carboxylic acid group of a salt thereof; and
 (c) optionally neutralizing said carboxylic acid group with an alkali metal or ammonium.

* * * * *

UNITED STATES PATENT AND TRADEMARK OFFICE
CERTIFICATE OF CORRECTION

PATENT NO. : 5,861,369
DATED : January 19, 1999
INVENTOR(S) : Charles Navarro

It is certified that error appears in the above-identified patent and that said Letters Patent is hereby corrected as shown below:

In claim 1, line 1 after the formula, "$R_4$-$R_5R_4$" should be "-$R_4$-$R_5$; $R_4$"

In claim 1, line 2 after the formula, "$C_r$-$C_{20}$" should be "$C_1$-$C_{20}$"

In claim 1, at column 7, line 2, "fura" should be "furyl"

In claim 1, at column 7, line 9, "($CO_2Z$) - $CH_2Z$" should be "($CO_2Z$) - $CH_2$-$CO_2$-Z."

In claim 15, 7 lines after the formula I, "-R4-R6" should be "-$R_4$-$R_6$"

In claim 15, line 8 after the formula I, "R6" should be "$R_6$"

In claim 15, line 9 after the formula I, "-CH(-$CO_2Z$)-$CH_2$-$CO_2Z$" should be "-CH($CO_2Z$)-$CH_2$-$CO_2Z$"

In claim 15, line 13 after formula I, "$CO_2Z$-$SO_3$" should be "$CO_2Z$, -$SO_3Z$"

Signed and Sealed this

Twenty-fifth Day of May, 1999

*Attest:*

Q. TODD DICKINSON

*Attesting Officer*     Acting Commissioner of Patents and Trademarks